United States Patent
Kikuchi et al.

(10) Patent No.: US 10,661,497 B2
(45) Date of Patent: May 26, 2020

(54) HEAT SHRINK TUBE AND METHOD FOR PRODUCING THE SAME

(71) Applicants: NISSEI ELECTRIC CO., LTD., Hamamatsu-shi, Shizuoka (JP); DUPONT-MITSUI FLUOROCHEMICALS CO., LTD., Minato-ku, Tokyo (JP)

(72) Inventors: Hideki Kikuchi, Hamamatsu (JP); Tetsuto Nakajima, Hamamatsu (JP); Daisuke Tanaka, Hamamatsu (JP); Takao Nishio, Shizuoka (JP); Etsuya Taki, Tokyo (JP); Hoai-Nam Pham, Shizuoka (JP)

(73) Assignees: NISSEI ELECTRIC CO., LTD., Hamamatsu-Shi, Shizuoka (JP); DUPONT-MITSUI FLUORCHEMICALS CO., LTD., Minato-Ku, Tokyo (JP)

( * ) Notice: Subject to any disclaimer, the term of this patent is extended or adjusted under 35 U.S.C. 154(b) by 404 days.

(21) Appl. No.: 15/736,180

(22) PCT Filed: Jun. 15, 2016

(86) PCT No.: PCT/JP2016/067776
§ 371 (c)(1),
(2) Date: Dec. 13, 2017

(87) PCT Pub. No.: WO2016/204174
PCT Pub. Date: Dec. 22, 2016

(65) Prior Publication Data
US 2018/0186062 A1    Jul. 5, 2018

(30) Foreign Application Priority Data
Jun. 16, 2015    (JP) ................. 2015-121181

(51) Int. Cl.
C08J 7/04    (2020.01)
B29C 61/08    (2006.01)
(Continued)

(52) U.S. Cl.
CPC ............ *B29C 61/08* (2013.01); *A61L 29/041* (2013.01); *A61L 29/049* (2013.01); *A61L 29/14* (2013.01);
(Continued)

(58) Field of Classification Search
CPC .................... C08J 3/005; B29C 43/02
(Continued)

(56) References Cited

U.S. PATENT DOCUMENTS

2006/0122333 A1    6/2006  Nishio
2008/0248226 A1    10/2008  Simon et al.
(Continued)

FOREIGN PATENT DOCUMENTS

JP    S48-34956 A    5/1973
JP    S 60-219027 A    11/1985
(Continued)

OTHER PUBLICATIONS

International Search Report (PCT/ISA/210) dated Jul. 26, 2016, by the Japan Patent Office as the International Searching Authority for International Application No. PCT/JP2016/067776.
(Continued)

*Primary Examiner* — Ellen S Hock
(74) *Attorney, Agent, or Firm* — Buchanan Ingersoll & Rooney PC (57) ABSTRACT

An object of the present invention is to provide a heat shrink tube excellent in peelability and transparency, and a method for producing the heat shrink tube. The present invention provides a peelable heat shrink tube comprising a composition containing a melt-processable fluororesin and PTFE,
(Continued)

the PTFE lacking a heat history of its melting point or higher after polymerization and having a specific gravity, as measured according to ASTM D4894, of 2.20 or less. The content of the PTFE is 0.05 to 3.0 wt % based on the total weight of the melt-processable fluororesin and the PTFE. The present invention also provides a method for producing the tube which comprises melt-extruding the composition at a temperature lower than the melting point of the PTFE.

14 Claims, 1 Drawing Sheet

(51) Int. Cl.
    *B29C 48/10*     (2019.01)
    *B29C 48/30*     (2019.01)
    *B29C 48/32*     (2019.01)
    *A61L 29/14*     (2006.01)
    *A61L 29/04*     (2006.01)
    *C08L 27/18*     (2006.01)
    *C08L 27/16*     (2006.01)
    *B29L 23/00*     (2006.01)
    *B29K 105/16*     (2006.01)
    *B29K 427/18*     (2006.01)
    *B29K 27/12*     (2006.01)
    *B29C 61/06*     (2006.01)
    *B29K 105/02*     (2006.01)

(52) U.S. Cl.
    CPC .............. *B29C 48/10* (2019.02); *B29C 48/30* (2019.02); *B29C 48/32* (2019.02); *C08L 27/16* (2013.01); *C08L 27/18* (2013.01); *B29C 61/06* (2013.01); *B29K 2027/12* (2013.01); *B29K 2105/02* (2013.01); *B29K 2105/16* (2013.01); *B29K 2427/18* (2013.01); *B29K 2995/0049* (2013.01); *B29L 2023/00* (2013.01); *C08L 2205/02* (2013.01); *C08L 2205/025* (2013.01)

(58) Field of Classification Search
    USPC ................................................ 428/34.1, 35.7
    See application file for complete search history.

(56) References Cited

U.S. PATENT DOCUMENTS

| | | |
|---|---|---|
| 2010/0197861 A1 | 8/2010 | Nishio |
| 2011/0223427 A1 | 9/2011 | Wano et al. |
| 2014/0255633 A1 | 9/2014 | Suzuki et al. |
| 2014/0287177 A1 | 9/2014 | Suda et al. |
| 2016/0317716 A1 | 11/2016 | Suzuki et al. |

FOREIGN PATENT DOCUMENTS

| | | |
|---|---|---|
| JP | 2006-159524 A | 6/2006 |
| JP | 2012-081590 A | 4/2012 |
| JP | 4968823 B2 | 7/2012 |
| JP | 2012-153766 A | 8/2012 |
| JP | 2013-71341 A | 4/2013 |
| JP | 5518268 B2 | 6/2014 |
| JP | 2014-129883 A | 7/2014 |
| JP | 2015-039843 A | 3/2015 |
| WO | 2008/007680 A1 | 1/2008 |

OTHER PUBLICATIONS

Written Opinion (PCT/ISA/237) dated Jul. 26, 2016, by the Japan Patent Office as the International Searching Authority for International Application No. PCT/JP2016/067776.

Notification of Reasons for Refusal issued by the Japanese Patent Office in corresponding Japanese Patent Application No. 2017-062210 dated Jan. 9, 2018 (6 pages including partial English translation).

Communication pursuant to Rule 164(1) EPC issued by the European Patent Office in corresponding European Patent Application No. 16811648.1-1014 dated Jan. 3, 2019 (11 pages).

$$DDR = \frac{D_D^2 - D_T^2}{D_O^2 - D_I^2}$$

HEAT SHRINK TUBE AND METHOD FOR PRODUCING THE SAME

TECHNICAL FIELD

This invention relates to a heat shrink tube, which comprises a fluororesin, excels in peelability, and has a high thermal (heat) shrinkage rate and high transparency, and a method for producing the heat shrink tube.

BACKGROUND ART

Fluororesins are excellent, for example, in chemical stability, heat resistance and mold release characteristics as compared with other plastics. Thus, heat shrink tubes made of fluororesins are used as protective and insulating heat shrink tubes in various fields including foods, medicine, pharmaceutics, chemistry, and analytical instruments.

Among uses as general heat shrink tubes for protective and insulating purposes are uses involving processing of products in which the heat shrink tube is once coated, if required, and then only the heat shrink tube is peeled off. They include, for example, uses in which electric wires, tubes, etc. having a multilayer structure including a protective layer for a blade or the like, or having a heteromorphic structure, are coated with the heat Shrink tube, and the interior members are molded or heat-welded, whereafter the heat shrink tube is removed.

In addition to the excellent properties characteristic of fluororesins, the excellent property of the tube being easily peeled and strippable by hand, namely, peelability, is required of such uses.

Patent Document 1 describes a peelable tube comprising a mixture of a plurality of thermoplastic fluororesins containing different types of fluororesins.

Patent Document 2 and Patent Document 3 show heat shrink tubes having peelability. These documents describe that fluororesins used therein are characterized by fulfilling the change amount of loss energy as specially defined; comprising a mixture of a plurality of fluororesins of different types; and containing a fluororesin accounting for a main proportion in the mixture (i.e., a main fluororesin), the main fluororesin being a polymer composed of at least three types of monomers, the polymer being a copolymer containing at least tetrafluoroethylene (TFE) and hexafluoropropylene (HFP) as its constituent monomers.

The heat shrink tubes of Patent Documents 2 and 3, however, tend to be excellent in peelability, but are decreased in shrinkage rate, as the amounts added of the fluororesins other than the main fluororesin increase. Depending on the uses they are put to, therefore, the amount of their heat shrinkage is insufficient, and they fail to fulfill the roles of heat shrink tubes, so that further improvements are required of them.

The present inventors have also found that the heat shrink tubes described in Patent Documents 1 to 3 show a tendency toward better peelability with increases in the amounts of the other fluororesins added, but pose the problem of decreased transparency such that they become cloudy, making it difficult to confirm the state of the underlying material through the heat-shrunk tube.

PRIOR ART DOCUMENTS

Patent Documents

Patent Document 1: Japanese Patent No. 4968823
Patent Document 2: Japanese Patent No. 5518268
Patent Document 3: JP-A-2014-129883

SUMMARY OF THE INVENTION

Problems to be Solved by the Invention

It is an object of the present invention to provide a heat shrink tube having the peelability of the publicly known heat shrink tubes and, in addition, improved in heat shrinkage rate, and excellent in transparency as well.

Means for Solving the Problems

The present invention provides a peelable heat shrink tube comprising a composition containing a melt-processable fluororesin and PTFE having no heat history of a melting point or higher after polymerization and having a specific gravity, as measured according to ASTM D4894, of 2.20 or less, wherein the content of the PTFE is 0.05 to 3.0 wt % based on the total weight of the melt-processable fluororesin and the PTFE.

The present invention provides a peelable heat shrink tube which is obtained by forming a composition at a temperature lower than the melting point of PTFE, wherein the composition contains a melt-processable fluororesin and the PTFE, the PTFE lacking a heat history of the melting point or higher after polymerization and having a specific gravity, as measured according to ASTM D4894, of 2.20 or less, the content of the PTFE being 0.05 to 3.0 wt % based on the total weight of the melt-processable fluororesin and the PTFE.

The heat shrink tube having a heat shrinkage rate of 40% or more is a preferred aspect of the present invention.

The heat shrink tube having transparency, that is, having a transmittance, as measured in compliance with ASTM D1746 using a transparency measuring instrument, of 80% or more is a preferred aspect of the present invention.

The present invention also provides a method for producing a peelable heat shrink tube, comprising: melt-extruding a composition at a temperature lower than the melting point of PTFE, wherein the composition contains a or melt-processable fluororesin and the PTFE, the PTFE lacking a heat history of the melting point or higher after polymerization and having a specific gravity, as measured according to ASTM D4894, of 2.20 or less, the content of the PTFE being 0.05 to 3.0 wt % based on the total weight of the melt-processable fluororesin and the PTFE.

The method for producing the peelable heat shrink tube, which comprises performing melt extrusion under such conditions that a drawdown ratio (DDR), as calculated from the following equation, is 20 to 300

$$DDR=(D_D^2-D_T^2)/(D_o^2-D_r^2)$$

where $D_D$ represents the inner diameter of a die, $D_T$ represents the outer diameter of a mandrel, $D_o$ represents the outer diameter of the tube, and $D_r$ represents the inner diameter of the tube is a preferred aspect of the present invention.

The method for producing the peelable heat shrink tube, which comprises premixing the melt-processable fluororesin and the PTFE, then melt-mixing the resulting mixture at a temperature lower than the melting point of the PTFE to obtain a pellet-shaped material containing the melt-processable fluororesin and the PTFE, and further melt-extruding the material at a temperature lower than the melting point of the PTFE, is a preferred aspect of the present invention.

Effects of the Invention

The hat shrink tube, and the method for producing it, according to the present invention, can be expected to show the following excellent effects:
(1) The peel strength of the tube in the longitudinal direction can be lowered. Thus, the tube can be easily peeled by hand, with a notch measuring several millimeters or so as a starting point.
(2) The heat shrinkage rate is 40% or more. Thus, clamping by the heat-shrunk tube is sufficiently ensured, a high work efficiency is obtained, and the tube can be put to any type of use.
(3) A peelable tube comprising PTFE and a small proportion of a low molecular weight fluororesin is known (e.g., Japanese Utility Model No. 2528627). Compared with such a publicly known tube, the content of PTFE is so low that rupture, cracking, or burst during diameter expansion of the tube does not occur. As a result, a sufficient heat shrinkage rate can be ensured, with peelability being maintained. That is, a heat shrink tube excellent in both of peelability and heat shrinkage rate is obtained.
(4) The content of PTFE is markedly low in comparison with the conventional technologies. Thus, the transparency of the heat-fusible resin is retained, and the state of the substrate below the heat-shrunk tube is easy to confirm.
(5) According to the method for production of the present invention, PTFE is uniformly dispersed and, starting therewith, peelability is exhibited. Thus, a tube having stable peelability over the continuous length is obtained.

MODE FOR CARRYING OUT THE INVENTION

Figure 1:
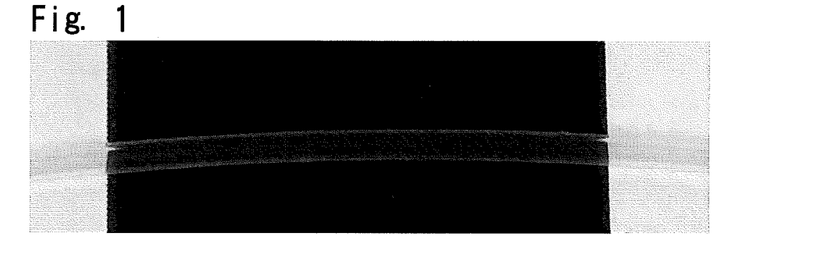
FIG. 1 is a photograph comparing the transparency of a heat shrink tube obtained in Example 3 of the present invention.
Figure 2:
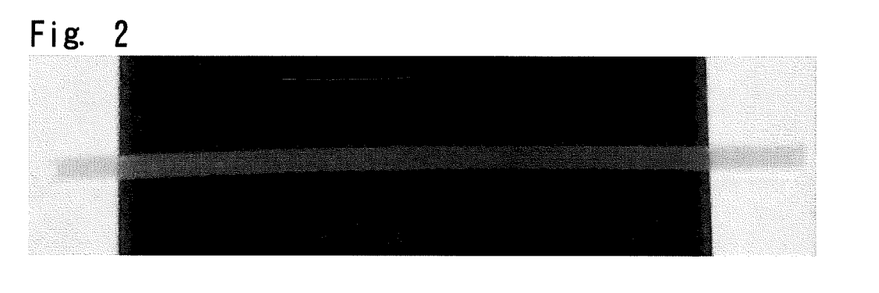
FIG. 2 is a photograph comparing the transparency of a heat shrink tube obtained by a conventional technology (Example 1 of Patent Document 1).
Figure 3:
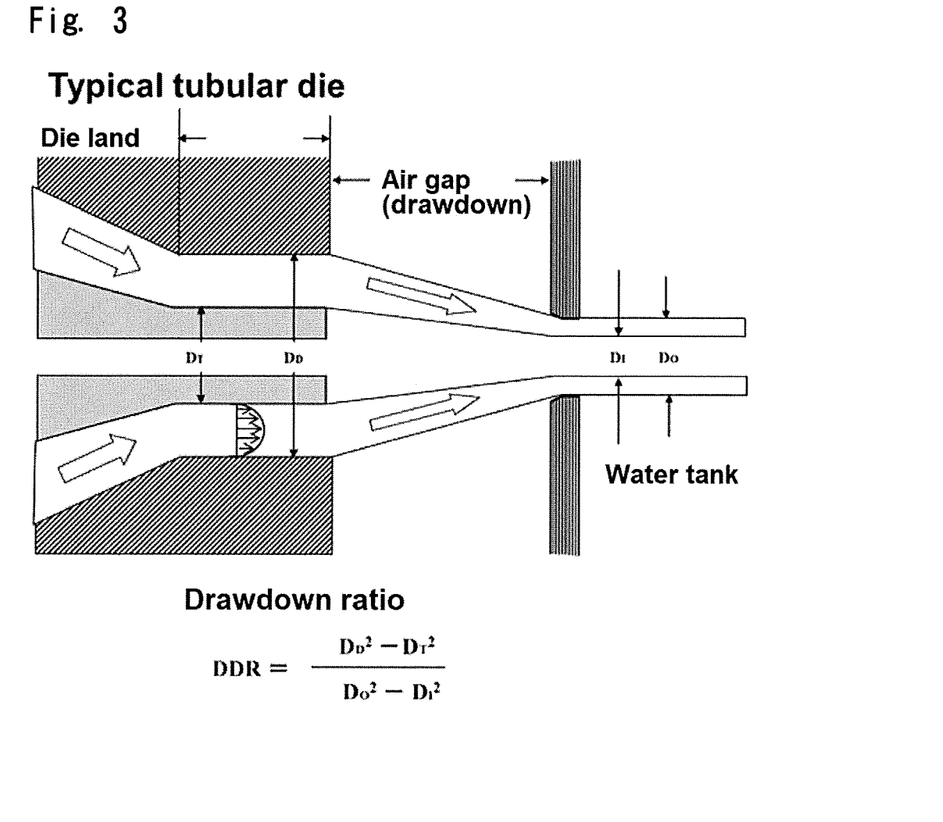
FIG. 3 is a view showing a typical tube extrusion die.

The peelable heat shrink tube of the present invention is obtained by melt-forming a composition at a temperature below the melting point of PTFE, the composition containing a melt-processable fluororesin and the PTFE lacking a heat history of the melting point or higher after polymerization and having a specific gravity, as measured according to ASTM D4894, of 2.20 or less.

The melt-forming technique is a forming method using a publicly known extruder. With this method, the composition is flowed in a molten state, whereby a formed product showing sufficient strength and durability suitable for a predetermined purpose, such as a film, fiber or tube, can be prepared from a melt.

Examples of the melt-processable fluororesin are copolymers melting at a temperature of a melting point or above to show fluidity. They include polymers or copolymers of unsaturated fluorinated hydrocarbons, unsaturated fluorinated chlorinated hydrocarbons, and ether group-containing unsaturated fluorinated hydrocarbons, etc., or copolymers of these unsaturated fluorinated hydrocarbons and ethylene. Their concrete examples include copolymers of tetrafluoroethylene and at least one monomer selected from hexafluoropropylene, fluoroalkoxytrifluoroethylene (preferably, perfluoroalkyl vinyl ether (hereinafter called PAVE)), chlorotrifluoroethylene, vinylidene fluoride, and vinyl fluoride; or copolymers of these monomers with ethylene. More concrete examples include tetrafluoroethylene-hexafluoropropylene copolymer (hereinafter, FEP), tetrafluoroethylene-perfluoroalkyl vinyl ether copolymer (hereinafter, PFA), tetrafluoroethylene-ethylene copolymer (hereinafter, ETFE), tetrafluoroethylene-hexafluoropropylene-vinylidene fluoride copolymer (hereinafter, THV), and polyvinylidene fluoride-polyvinylidene difluoride (hereinafter, PVDF).

Preferred examples of the melt-processable fluororesin, from the viewpoint of transparency, include FEP composed two monomers (i.e., a copolymer of TFE and HFP). Other examples are mixtures of FEP with different melting points, and mixtures of FEP and melt-processable fluororesins different from FEP.

The melt-processable fluororesins may be used alone, or may be mixtures of two or more of them. Also available are mixtures of at least two of the same type of copolymer different in the type of comonomer, comonomer content, molecular weight (weight average molecular weight or number average molecular weight), molecular weight distribution, melting point, melt flow rate (MFR), or the like, or different in mechanical properties. Their examples include mixtures of PFAs or FEPs. Such melt-processable fluororesins can be produced by a publicly known method such as solution polymerization, emulsion polymerization, or suspension polymerization.

The melt flow rate (MFR) of the melt-processable fluororesin is preferably 1 to 100 g/10 min, more preferably 1 to 80 g/10 min, and further preferably 1 to 50 g/10 min. The MFR is measured at a temperature of 372° C. under a load of 5 kg in accordance with ASTM D1238-95.

The MFR affects the degree of orientation of PTFE due to its fiberization to be described later. The lower the MFR, the higher the degree of orientation becomes, and there is a tendency to obtain a tube better in peelability.

The melting point of the melt-processable fluororesin is not limited, as long as it is within a range where a tube can be formed. However, it is 150° C. or higher, preferably in the range of 150 to 320° C.

The melting point of the melt-processable fluororesin is lower than the melting point of PTFE and, for the purpose of preventing compatibilization, is preferably different greatly from the melting point of PTFE.

An example of the PTFE is a polymer of tetrafluoroethylene (TFE) alone, called a homopolymer of tetrafluoroethylene (PTFE), or a copolymer of tetrafluoroethylene containing 1% or less of a comonomer (i.e., modified PTFE). The melting point of the PTFE immediately after polymerization is 336 to 343° C., depending on the method of polymerization.

The polymerization method for the PTFE can be a publicly known method such as solution polymerization, emulsion polymerization, or suspension polymerization. The preferred resulting PTFE is preferably a fine powder with an average particle size of 300 to 600 μm obtained by coagulating and drying a polymer latex produced by emulsion polymerization.

Such PTFE does not exhibit melt formability, and is present in a composition (or in pellets) in the state of polymer particles which undergo orientation due to fiberization by a shearing force and/or a stretching force during melt extrusion of the tube.

The PTFE of the present invention is preferably PTFE obtained as above which does not have a heat history of the melting point or higher after polymerization and which has a specific gravity, as measured according to ASTM D4894, of 2.20 or less.

Heating the PTFE to the melting point or above after polymerization is not preferred. This is because the molecular chains of crystals of the PTFE arranged neatly are loosened by molecular relaxation, and the molecules are apt to be entangled randomly, thus posing difficulty with fiberization. Another reason is that the melting point of the PTFE is lowered, and its difference from the melting point of the melt-processable fluororesin tends to be small.

Since the PTFE having no heat history of the melting point or higher after polymerization and having a specific gravity of 2.20 or less is high-molecular weight, it is easy to fiberize. By using such PTFE, therefore, the PTFE is fiberized by a shearing force and/or a stretching force during melt extrusion for tube production, and orientation takes place in the direction of tube extrusion, so that the resulting tube can possess peelability.

The content of the PTFE in the composition containing the melt-processable fluororesin and the PTFE in the present invention is 0.05 to 3.0 wt % based on the total weight of the melt-processable fluororesin and the PTFE. If the PTFE content is in the range of 0.05 to 3.0 wt %, rupture, cracking, or burst does not occur during diameter expansion. The resulting tube is excellent in peelability, can be peeled easily by hand, and has a heat shrinkage rate of 40% or more and high work efficiency. The PTFE content is more preferably 0.2 to 1.0 wt %, because the resulting tube is excellent in peelability, and has a heat shrinkage rate of 40% or more, preferably 50% or more, demonstrating high work efficiency; that is, the tube is excellent in both of peelability and heat shrinkage.

The method of mixing these materials, in preparation for forming the composition containing the melt-processable fluororesin and the PTFE into a tubing shape, can be performed upon appropriate selection from the publicly known methods. Its examples will be shown below.

The examples of the mixing method include a method of obtaining the composition containing the melt-processable fluororesin and the PTFE by premixing, and a method which comprises further melt-mixing the premixed composition at a temperature lower than the melting point of the PTFE to obtain a material in the form of pellets.

The method of premixing the composition containing the melt-processable fluororesin and the PTFE may be a publicly known method such as dry mixing or wet mixing. For example, the premixing can be performed using a publicly known dispersing or mixing machine or method such as a coaggregation method, a planetary mixer, a highspeed impeller disperser, a rotary drum mixer, a screw mixer, a belt conveyor mixing, a ball mill, a pebble mill, a sand mill, a roll mill, an attritor, or a bead mill. A device capable of uniform dispersion is more preferred.

The forms of the melt-processable fluororesin and the PTFE for use in mixing are not limited. However, a dispersion of fine particles having an average particle size of 0.05 to 1 μm, a powdery material measuring several to several tens of micrometers, or granules of a powder measuring several hundred micrometers can be named in consideration of work efficiency.

The form of the composition according to the present invention is, for example, a powder, granules of a powder, particles, flakes, or pellets. The average particle size of the resulting composition is 0.1 μm or more, and is preferably in such a range as not to impair handleability.

Usable as a method for obtaining the pellet-shaped material is a publicly known method, for example, comprising melt-extruding the composition by means of a single screw or twin-screw extruder to form a strand (string-shaped material), then cooling the strand, and cut it into predetermined lengths to form pellets. The melt extrusion temperature is preferably a temperature which is equal to or higher than the melting point of the melt-processable fluororesin, but is lower than the melting point of the PTFE. By setting the temperature lower than the melting point of the PTFE, a fall in the melting point of the PTFE can be prevented, and a highly crystalline state (a state facilitating fiberization) immediately after polymerization can be maintained. Consequently, when the composition is melt-extruded into a tubing form in a subsequent step, the PTFE can be fiberized and oriented by a shearing force and/or a stretching force.

Cutting into the predetermined lengths can be performed using a publicly known method such as strand cutting, hot cutting, or underwater cutting. The average particle size of the pellet-shaped material is 0.1 mm or more, and is preferably in such a range as not to impair handleability.

The mixing method is not limited to those mentioned above, and a preferred method for obtaining more stable peelability over a continuous length is used.

Next, an example of the method for melt-extruding the heat shrink tube of the present invention will be shown.

The above-mentioned composition or pellet-shaped composition prepared in advance is melt-extruded into a tubing form at a temperature below the melting point of the PTFE. Since kneading within a cylinder of a melt extruder is apt to cause fiberization of the PTFE, the temperature of the cylinder (screw) of the melt extruder is equal to or lower than the melting point of the PTFE. From the viewpoint of formability and productivity, on the other hand, only the temperature of the die portion of the melt extruder, which is minimally affected by kneading (where the fiberization of the PTFE minimally occurs), can be rendered equal to or higher than the melting point of the PTFE for such a short period of time that the inhibition of peelability due to the entanglement of the PTFE molecular chains does not occur.

The forming temperature in the present invention is lower than the melting point of the PTFE. Thus, the state free from the entanglement of the PTFE molecular chains is maintained until extrusion into the tubing form out of the die of the extruder. Under a shearing force and/or a stretching force in the subsequent formation (cooling) step, the PTFE is fiberized and oriented. Within the resulting solidified tube, a state where the melt-processable fluororesin and the PTFE are not compatible, namely, a state where the molecular orientation of the PTFE is great, is existent, so that the tube can be peeled easily, with such a state serving as a starting point.

If a temperature of the PTFE becomes equal to or higher than the melting point during melt extrusion, the molecular chains of the PTFE are apt to become entangled with the molecular chains of the melt-processable fluororesin because of molecular relaxation. As a result, the molecular chains of the PTFE are fiberized with difficulty, or are not fiberized. This brings out the drawback that the molecular orientation effect of the PTFE is not obtained, and peelability worsens.

Whether the heat history of the PTFE within the tube is present or not can be confirmed by calculating a melt tension ratio. The melt tension ratio is calculated from the following equation based on melt tension (unit: g) measured using a capillary rheometer (Capilograph Model 1D, produced by TOYO SEIKI Co., Ltd.):

Melt tension ratio=melt tension at 340° C./melt tension at 320° C.

The melt tension was determined in the following manner using the above capillary rheometer: The cylinder with a measuring temperature stabilized at 320° C. or 340° C. was charged with 30 g of a sample for measurement. After the sample was allowed to dwell for 10 minutes, a strand was extruded at a piston speed of 3 mm/min from an orifice of 2 mm in diameter by 20 mm in length. The strand was taken up by means of a melt tension measuring roll at a take-up speed of 5 m/min to measure the melt tension. Measurements at each measuring temperature were made 5 times, and the average of the measured values was taken as the melt tension at 320° C. or 340° C.

The melt tension shows the presence or absence of the heat history of the PTFE.

Generally, the melt tension tends to decrease upon heating. However, when the PTFE is heated to the melting point or higher after polymerization, the molecular chains of the crystals of the PTFE arranged neatly are loosened by molecular relaxation, and their random entanglement occurs, so that the melt tension increases.

Hence, the fact that the melt tension measured at the melting point of the PTFE (320° C.) or lower is high means that PTFE having a heat history of the melting point or higher after polymerization is contained. Since its value is higher than when PTFE without a heat history of the melting point or higher after polymerization is contained, the melt tension ratio becomes low.

That is, when the melt-processable fluororesin composition containing PTFE having a heat history of the melting point or higher after polymerization is subject to forming at a temperature below the melting point of PTFE, or when the composition is subject to forming at the melting point (340° C.) of PTFE or higher, the melt tension ratio becomes low. Based on these findings, whether the heat history of PTFE has been present or absent can be confirmed.

|  | PTFE without a heat history of the melting point or higher after polymerization is contained | PTFE having a heat history of the melting point or higher after polymerization is contained |
| --- | --- | --- |
| Melt tension ① (320° C.) | Low | High |
| Melt tension ② (340° C.) | High | High |
| Melt tension ratio (②/①) | High (high/low) | Low (high/high) |

The melt tension ratio in the present invention is 0.8 or higher, preferably 1.0 or higher, and more preferably 1.5 or higher. Desirably, the melt tension ratio is 30 or lower. When the melt tension ratio is 0.8 or higher, but 30 or lower, the peelability of the resulting tube is increased, because the PTFE has no heat history and is moderately oriented. Furthermore, the diameter of the tube can be greatly increased, without rupture of the tube, during diameter expansion of the tube. In addition, diameter expansion and extrusion of the tube can be performed at a faster speed, thus increasing productivity.

If the melt tension ratio is less than 0.7, on the other hand, PTFE has a heat history, and molecular chain entanglement of the PTFE and the melt-processable fluororesin occurs. Since the PTFE is minimally oriented or is not oriented, peelability becomes poor. If the melt tension ratio exceeds 30, the degree of orientation of the PTFE is so high that uniform expansion of the tube diameter is difficult, thus deteriorating dimensional accuracy. This is also undesirable.

Thus, a forming material comprising a composition, which contains the melt-processable fluororesin and the PTFE and has a melt tension ratio of 0.8 to 30, is a preferred forming material for obtaining the heat shrink tube of the present invention.

By melt-extruding such a forming material, the heat shrink tube of the present invention can be obtained.

The formed tube is heated and internally pressurized for diameter expansion, whereby it is turned into the heat shrink tube of the present invention.

A diameter expansion rate E is represented by the following equation and, preferably, the diameter expansion rate E is, although not limited to, 200% or less:

$$E(\%)=(Y-X)/X \times 100$$

(X: dimension of melt-extruded tube
Y: dimension of tube after diameter expansion)

The diameter expansion rate correlates with the heat shrinkage rate, and an increase in the diameter expansion rate contributes to an increase in the work efficiency. If the increase is too great, however, the expanded tube tends to minimally return to the outer diameter before diameter expansion, and the work efficiency is aggravated. Thus, a diameter expansion rate of 50 to 150% can be said to be a further preferred range.

The heat shrinkage rate S is represented by the following equation. The heat shrinkage rate S is preferably 40% or more, more preferably 50% or higher.

$$S(\%)=(P-Q)/P \times 100$$

(P: dimension of tube after diameter expansion processing
Q: dimension of tube after shrinkage)

As the heat shrinkage rate increases, sufficient clamping by the heat-shrunk tube is obtained. Thus, excellent workability results, so that the tube can be put to every usage. As the tube is shrunk at a higher temperature, the shrinkage rate becomes greater. To obtain a greater shrinkage rate, therefore, a method of shrinking the tube at a high temperature in a short time is also available. In this case, the shrinking temperature needs to be determined in consideration of the heat resistance of the material to be coated.

The heat shrink tube of the present invention is characterized in that it retains a high thermal (heat) shrinkage rate, namely, a high work efficiency, and excels in contradictory properties, i.e., peelability.

The melt extrusion method for the heat shrink tube of the present invention provides a drawdown ratio (DDR), as calculated from the following equation, of 10 to 500, preferably 20 to 300, more preferably 20 to 200.

$$DDR=(D_D^2-D_T^2)/(D_o^2-D_r^2)$$

where $D_D$ represents the inner diameter of a die, $D_T$ represents the outer diameter of a mandrel, $D_o$ represents the outer diameter of the tube, and $D_r$ represents the inner diameter of the tube.

As the drawdown ratio increases, the resulting tube is higher in the degree of orientation of PTFE due to fiberization, and is better in peelability.

The peel strength in the longitudinal direction of the heat shrink tube of the present invention is preferably 6.0 N or less. With the peel strength of 6.0 N or less, the tube can be easily peeled by hand, starting in a notch measuring several millimeters or so.

The peel strength is measured based on the following method:

A 20 mm notch is provided near the center of the diameter at one end of a measurement sample measuring 100 mm, and the bifurcated notched parts are held by chucks (fixing jigs) of a tensile tester.

The notched parts of the measurement samples are further peeled at a tension speed of 100 mm/min, and maximum strength under these conditions is measured. The average value of the measurements (n=5) is used as peel strength.

The peelability is exhibited, with the oriented site of the fiberized PTFE serving as a starting point. Thus, the peelability can be evaluated in the measurement of the degree of orientation as well.

The degree of orientation is measured based on the following method:

The degree of orientation (degree of fiberization) of PTFE in the heat shrink tube due to fiberization was measured using an X-ray diffraction device (RINT2550 Model WAXD, manufactured by Rigaku Corporation). The device used an X-ray source for CuKα and a detector of a scintillation counter, and made measurements at outputs of 40 kV and 370 mA. The sample tube was cut open, and used as a measurement sample. The measurement sample was fixed to a sample holder, with the longitudinal direction of the sample as a reference axis, and fluororesin-derived peaks near 2θ=18° were measured for the azimuth angle distribution strength.

The degree of orientation was calculated from the following equation. The higher the value of the degree of orientation, the more intense the orientation of crystallites is.

Degree of orientation=(180−β)/180 (β is the half-value width of the orientation-derived peak)

In regard to the transparency of the heat shrink tube of the present invention, the tube has a transmittance of 80% or more, particularly preferably 90% or more. The transmittance is measured by a method complying with ASTM D1746 with the use of a commercially available transparency measuring instrument.

The heat shrink tube of the present invention is excellent in both of peelability and heat shrinkage rate, and also excels in transparency. Thus, it is useful in foods, medicine, pharmaceutics, chemistry, analytical instruments, and any other technical field. The tube is particularly useful for uses in which electric wires, tubes, etc. having a multilayer structure including a protective layer for a blade or the like, or having a heteromorphic structure, are coated with the heat shrink tube, and interior members are molded or heat-welded, whereafter the heat shrink tube is removed.

EXAMPLES

The present invention will now be described in more detail by way of Examples, but is not limited at all by these Examples.

Example 1

FEP (Teflon (registered trademark) FEP100J, produced by Du Pont-Mitsui Fluorochemicals Co., Ltd., MFR 7 g/10 min, melting point 260° C.) comprising two types of monomers (i.e., a copolymer of TFE and HFP) was used as a melt-processable fluororesin. A PTFE powder (melting point 336° C.) lacking a heat history of the melting point thereof or higher after polymerization and having a specific gravity of 2.20 was mixed in an amount of 0.05 wt % with the heat-fusible resin. The resulting mixture was formed into pellets at a extruding temperature of 320° C. (a temperature lower than the melting point of PTFE). The pellets were melt-extruded (DDR=110) in the form of a tube at a extruding temperature of 320° C. (a temperature lower than the melting point of PTFE) by means of a melt extruder. The resulting tube was 1.2 mm in inner diameter and 1.6 mm in outer diameter.

The forming temperature represents the temperature of the molten resin within the melt extruder.

The tube was heated and internally pressurized for diameter expansion, whereby a heat shrink tube was obtained.

Example 2

A heat shrink tube was obtained in the same manner as in Example 1, except that the content of PTFE was set at 0.2 wt %.

Example 3

A heat shrink tube was obtained in the same manner as in Example 1, except that the content of PTFE was set at 0.4 wt %.

Example 4

A heat shrink tube was obtained in the same manner as in Example 1, except that the content of PTFE was set at 0.6 wt %.

Example 5

A heat shrink tube was obtained in the same manner as in Example 1, except that the content of PTFE was set at 1.0 wt %.

Example 6

A heat shrink tube was obtained in the same manner as in Example 1, except that the content of PTFE was set at 2.0 wt %.

Example 7

A heat shrink tube was obtained in the same manner as in Example 1, except that the content of PTFE was set at 3.0 wt %.

Example 8

A heat shrink tube was obtained in the same manner as in Example 3, except that FEP (Teflon (registered trademark) FEP140J, produced by Du Pont-Mitsui Fluorochemicals Co., Ltd., MFR 3 g/10 min, melting point 260° C.) comprising two types of monomers (i.e., a copolymer of TFE and HFP) was used as a melt-processable fluororesin, and pellets were formed at a extruding temperature of 300° C. (a temperature lower than the melting point of PTFE).

Example 9

A heat shrink tube was obtained in the same manner as in Example 3, except that FEP (Teflon (registered trademark) FEP9494-J, produced by Du Pont-Mitsui Fluorochemicals Co., Ltd., MFR 30 g/10 min, melting point 260° C.) comprising three types of monomers (i.e., a TFE/HFP/PAVE terpolymer) was used as a melt-processable fluororesin, and pellets were formed at a extruding temperature of 300° C. (a temperature lower than the melting point of PTFE).

Example 10

A heat shrink tube was obtained in the same manner as in Example 3, except that PFA (Teflon (registered trademark) PFA920HP Plus, produced by Du Pont-Mitsui Fluorochemicals Co., Ltd., MFR 30 g/10 min, melting point 280° C.) comprising two types of monomers (i.e., a copolymer of TFE and PAVE) was used as a melt-processable fluororesin, and pellets were formed at a extruding temperature of 300° C. (a temperature lower than the melting point of PTFE).

Example 11

A heat shrink tube was obtained in the same manner as in Example 1, except that pellets were formed at a extruding temperature of 300° C. (a temperature lower than the melting point of PTFE).

Example 12

A heat shrink tube was obtained in the same manner as in Example 2, except that pellets were formed at a extruding temperature of 300° C. (a temperature lower than the melting point of PTFE).

Example 13

A heat shrink tube was obtained in the same manner as in Example 3, except that pellets were formed at a extruding temperature of 300° C. (a temperature lower than the melting point of PTFE).

Example 14

A heat shrink tube was obtained in the same manner as in Example 4, except that pellets were formed at a extruding temperature of 300° C. (a temperature lower than the melting point of PTFE).

Example 15

A heat shrink tube was obtained in the same manner as in Example 5, except that pellets were formed at a extruding temperature of 300° C. (a temperature lower than the melting point of PTFE).

Comparative Example 1

A heat shrink tube was obtained in the same manner as in Example 1, except that the content of PTFE was set at 0.03 wt %.

Comparative Example 2

A heat shrink tube was obtained in the same manner as in Example 1, except that the content of PTFE was set at 3.5 wt %.

Comparative Example 3

A heat shrink tube was obtained in the same manner as in Example 1, except that the content of PTFE was set at 0.0 wt %.

Comparative Example 4

FEP (Teflon (registered trademark) FEP100J, produced by Du Pont-Mitsui Fluorochemicals Co., Ltd., MFR 7 g/10 min, melting point 260° C.) comprising two types of monomers (i.e., a copolymer of TFE and HFP) was used as a melt-processable fluororesin. A PTFE powder (melting point 336° C.) lacking a heat history of the melting point thereof or higher after polymerization and having a specific gravity of 2.20 was mixed in an amount of 0.4 wt % with the melt-processable fluororesin. The resulting mixture was formed into pellets at a extruding temperature of 340° C. (a temperature higher than the melting point of PTFE). The pellets were used as a sample.

The heat shrink tubes of the above-mentioned Examples and Comparative Examples were evaluated for peel strength, heat shrinkage rate, transparency, and degree of orientation. The results of the evaluations are shown in Table 1.

Moreover, the pellets of Examples 8 to 15 and Comparative Examples 3 and 4 were used to measure melt tension, and the melt tension ratio was calculated. The results are shown in Table 2.

(Evaluation Criteria for Peelability)

The peel strength was measured by the aforementioned method, and the results of the measurements were evaluated based on the following criteria:
⊚: Not less than 1500 mm was peelable easily.
◯: Not less than 1000 mm was peelable easily.
Δ: Slightly difficult to tear, but not less than 800 mm was peelable manually.
Represents the limiting value of a conforming article.
x: Manually peeled, but in some cases, the resin was broken halfway, and the tear distance shortened.

TABLE 1

| | | PTFE content [wt %] | Tear Strength | Peel-ability [N] | Heat shrink-age rate [%] | Trans-parency [%] | Degree of ori-entation |
|---|---|---|---|---|---|---|---|
| Example | 1 | 0.05 | ◯ | 6.0 | 59 | ≥80 | 0.53 |
| | 2 | 0.2 | ⊚ | 4.5 | 57 | ≥80 | 0.76 |
| | 3 | 0.4 | ⊚ | 3.0 | 55 | ≥80 | 0.82 |
| | 4 | 0.6 | ⊚ | 2.8 | 52 | ≥80 | 0.87 |
| | 5 | 1.0 | ⊚ | 2.6 | 51 | ≥80 | 0.89 |
| | 6 | 2.0 | ⊚ | 2.2 | 45 | ≥80 | 0.90 |
| | 7 | 3.0 | ⊚ | 2.0 | 41 | ≥80 | 0.92 |
| | 8 | 0.4 | ⊚ | 4.1 | 59 | ≥80 | 0.87 |
| | 9 | 0.4 | ⊚ | 3.7 | 56 | ≥80 | 0.84 |
| | 10 | 0.4 | ⊚ | 2.6 | 55 | ≥80 | 0.92 |
| | 11 | 0.05 | ◯ | 5.6 | 58 | ≥80 | 0.55 |
| | 12 | 0.2 | ⊚ | 4.2 | 56 | ≥80 | 0.78 |
| | 13 | 0.4 | ⊚ | 2.8 | 53 | ≥80 | 0.85 |
| | 14 | 0.6 | ⊚ | 2.4 | 50 | ≥80 | 0.88 |
| | 15 | 1.0 | ⊚ | 2.1 | 49 | ≥80 | 0.90 |
| Comparative Example | 1 | 0.03 | Δ | — | 63 | ≥80 | 0.50 |
| | 2 | 3.5 | ⊚ | 1.8 | 33 | <80 | 0.93 |
| | 3 | 0.0 | X | — | 65 | ≥80 | 0.46 |

TABLE 2

| | | PTFE content [wt %] | Melt tension (g) 320° C. | Melt tension (g) 340° C. | Melt tension ratio |
|---|---|---|---|---|---|
| Example | 8 | 0.4 | 10.09 | 24.10 | 2.39 |
| | 9 | 0.4 | 1.94 | 18.87 | 9.53 |
| | 10 | 0.4 | 1.64 | 14.45 | 8.80 |
| | 11 | 0.1 | 4.59 | 6.22 | 1.35 |

TABLE 2-continued

| | | PTFE content [wt %] | Melt tension (g) 320° C. | Melt tension (g) 340° C. | Melt tension ratio |
|---|---|---|---|---|---|
| | 12 | 0.2 | 6.10 | 14.15 | 2.37 |
| | 13 | 0.4 | 8.22 | 18.80 | 2.29 |
| | 14 | 0.6 | 8.75 | 29.82 | 3.41 |
| | 15 | 1.0 | 9.34 | 40.78 | 4.36 |
| Comparative | 3 | 0.0 | 4.52 | 3.05 | 0.67 |
| Example | 4 | 0.4 | 19.76 | 13.72 | 0.69 |

The heat shrink tubes of Examples 1 to 15 of the present invention are all excellent in peelability and have a high thermal (heat) shrinkage rate.

In particular, the heat shrink tubes of Examples 2 to 5 and Examples 12 to 15, namely, those having a PTFE content of 0.2 to 1.0 wt %, excel in peelability and have an excellent heat shrinkage rate of 50% or more, demonstrating that they possess both of these characteristics.

In Examples 1 and 11, that is, with a PTFE content close to the lower limit, peelability is slightly poor, but the heat shrinkage rate tends to be high.

In Example 7, that is, with a PTFE content close to the upper limit, peelability is excellent, but the heat shrinkage rate tends to be low.

The heat shrink tube of Comparative Example 1 has a PTFE content of lower than 0.05%, and is unusable from the viewpoint of peelability.

The heat shrink tube of Comparative Example 2 has a high PTFE content exceeding 3.0% and, during processing for diameter expansion, rupture, cracking, or burst, for example, occasionally occurs. Thus, the heat shrinkage rate has to be lowered. As a result, sufficient clamping by the heat-shrunk tube is not obtained, its uses are limited, and its work efficiency deteriorates. Thus, this heat shrink tube is not usable.

In the heat shrink tube of Comparative Example 3, that is, one with a PTFE content of 0.0%, the degree of orientation is lower than 0.5. As will be clear from comparisons with the Examples as well, the degree of orientation which enables the fiberization of PTFE to appear, contributing to an increase in peelability, is 0.50 or more.

As noted above, the heat shrink tube according to the present invention is found to be a heat shrink tube, which ensures a sufficient heat shrinkage rate, while maintaining peelability, thus excels in both of peelability and heat shrinkage rate, and is also excellent in transparency, as compared with the conventional technologies.

INDUSTRIAL APPLICABILITY

The heat shrink tube of the present invention is excellent in both of the characteristics, peelability and heat shrinkage rate, and also excels in transparency. Thus, it is useful in foods, medicine, pharmaceutics, chemistry, analytical instruments, and any other technical field.

The invention claimed is:

1. A peelable heat shrink tube which is obtained by forming a composition at a temperature lower than a melting point of polytetrafluoroethylene (PTFE),
wherein the composition contains a melt-processable fluororesin and the PTFE, the PTFE lacking a heat history of the melting point or higher after polymerization and having a specific gravity, as measured according to ASTM D4894, of 2.20 or less, a content of the PTFE being 0.05 to 3.0 wt % based on a total weight of the melt-processable fluororesin and the PTFE.

2. The peelable heat shrink tube according to claim 1, which has a heat shrinkage rate of 40% or more.

3. The peelable heat shrink tube according to claim 1, which has a transmittance, as measured in compliance with ASTM D1746 using a transparency measuring instrument, of 80% or more.

4. The peelable heat shrink tube according to claim 1, wherein
the melt-processable fluororesin is at least one copolymer selected from tetrafluoroethylene-hexafluoropropylene copolymer (FEP), tetrafluoroethylene-perfluoroalkyl vinyl ether copolymer (PFA), tetrafluoroethylene-ethylene copolymer (ETFE), tetrafluoroethylene-hexafluoropropylene-vinylidene fluoride copolymer (THV), and polyvinylidene fluoride-polyvinylidene difluoride (PVDF).

5. A method for producing a peelable heat shrink tube, comprising:
melt-extruding a composition at a temperature lower than a melting point of PTFE,
wherein the composition contains a melt-processable fluororesin and the PTFE, the PTFE lacking a heat history of the melting point or higher after polymerization and having a specific gravity, as measured according to ASTM D4894, of 2.20 or less, a content of the PTFE being 0.05 to 3.0 wt % based on a total weight of the melt-processable fluororesin and the PTFE.

6. The method for producing a peelable heat shrink tube according to claim 5, further comprising:
performing melt extrusion under such conditions that a drawdown ratio (DDR), as calculated from the following equation, is 20 to 300

$$DDR=(D_D^2-D_T^2)/(D_o^2-D_r^2)$$

where $D_D$ represents an inner diameter of a die, $D_T$ represents an outer diameter of a mandrel, $D_o$ represents an outer diameter of the tube, and $D_r$ represents an inner diameter of the tube.

7. The method for producing a peelable heat shrink tube according to claim 5, further comprising:
premixing the melt-processable fluororesin and the PTFE;
then melt-mixing a resulting mixture at a temperature lower than the melting point of the PTFE to obtain a pellet-shaped material containing the melt-processable fluororesin and the PTFE; and
further melt-extruding the material at a temperature lower than the melting point of the PTFE.

8. A forming material comprising a composition containing a melt-processable fluororesin and PTFE, the composition having a melt tension ratio of 0.8 or higher, but 30 or lower.

9. A heat shrink tube which is obtained by melt-extruding the forming material according to claim 8.

10. The peelable heat shrink tube according to claim 2, which has a transmittance, as measured in compliance with ASTM D1746 using a transparency measuring instrument, of 80% or more.

11. The peelable heat shrink tube according to claim 10, wherein
the melt-processable fluororesin is at least one copolymer selected from tetrafluoroethylene-hexafluoropropylene copolymer (FEP), tetrafluoroethylene-perfluoroalkyl vinyl ether copolymer (PFA), tetrafluoroethylene-ethylene copolymer (ETFE), tetrafluoroethylenehexafluoropropylene-vinylidene fluoride copolymer (THV), and polyvinylidene fluoride-polyvinylidene difluoride (PVDF).

12. The peelable heat shrink tube according to claim 3, wherein
the melt-processable fluororesin is at least one copolymer selected from tetrafluoroethylene-hexafluoropropylene copolymer (FEP), tetrafluoroethylene-perfluoroalkyl vinyl ether copolymer (PFA), tetrafluoroethylene-ethylene copolymer (ETFE), tetrafluoroethylene-hexafluoropropylene-vinylidene fluoride copolymer (THV), and polyvinylidene fluoride-polyvinylidene difluoride (PVDF).

13. The peelable heat shrink tube according to claim 2, wherein
the melt-processable fluororesin is at least one copolymer selected from tetrafluoroethylene-hexafluoropropylene copolymer (FEP), tetrafluoroethylene-perfluoroalkyl vinyl ether copolymer (PFA), tetrafluoroethylene-ethylene copolymer (ETFE), tetrafluoroethylene-hexafluoropropylene-vinylidene fluoride copolymer (THV), and polyvinylidene fluoride-polyvinylidene difluoride (PVDF).

14. The method for producing a peelable heat shrink tube according to claim 6, further comprising:
premixing the melt-processable fluororesin and the PTFE;
then melt-mixing a resulting mixture at a temperature lower than the melting point of the PTFE to obtain a pellet-shaped material containing the melt-processable fluororesin and the PTFE; and
further melt-extruding the material at a temperature lower than the melting point of the PTFE.

* * * * *